United States Patent [19]

Hamade et al.

[11] Patent Number: 6,150,146
[45] Date of Patent: Nov. 21, 2000

[54] METHOD FOR CONTROLLED RELEASE OF COMPOUNDS HAVING ANTIMICROBIAL ACTIVITY AND COATING COMPOSITION

[75] Inventors: Ryoji Hamade, Kadoma; Naoki Yamamori, Kyotanabe, both of Japan

[73] Assignee: Nippon Paint Co., Ltd., Osaka, Japan

[21] Appl. No.: 09/042,570

[22] Filed: Jan. 17, 1998

[30] Foreign Application Priority Data

Mar. 17, 1997 [JP] Japan .................................. 9-084505

[51] Int. Cl.$^7$ .............................. C12P 7/02; C12P 13/00; C12P 7/40; C12N 9/18; A61K 31/74
[52] U.S. Cl. .................. 435/155; 435/128; 435/136; 435/197; 435/212; 424/78.09
[58] Field of Search .................... 435/128, 132, 435/136, 155, 189, 192, 197, 212; 106/14.34; 424/78.09

[56] References Cited

U.S. PATENT DOCUMENTS

| 4,297,137 | 10/1981 | Sachetto et al. | 514/493 |
| 5,262,151 | 11/1993 | Montgomery | 424/50 |
| 5,770,188 | 6/1998 | Hamade et al. | 424/78.09 |
| 5,801,226 | 9/1998 | Cummins et al. | 530/388.2 |
| 5,919,689 | 7/1999 | Selvig et al. | 435/202 |
| 5,998,200 | 12/1999 | Bonaventura et al. | 435/264 |

FOREIGN PATENT DOCUMENTS

| 0 518 445 A1 | 12/1992 | European Pat. Off. . |
| 04337369 | 5/1991 | Japan . |
| 04279677 | 10/1992 | Japan . |
| 95/27009 | 10/1995 | WIPO . |
| 96/38548 | 12/1996 | WIPO . |

OTHER PUBLICATIONS

Kennedy et al. J. Chem. Soc. Perkin Trans. 1 (1978) 9: 1058–66 (abstract only).

Primary Examiner—Jon P. Weber
Attorney, Agent, or Firm—Pollock, Vande Sande & Amernick

[57] ABSTRACT

A novel method for controlled release of compounds having antimicrobial activity and a novel coating composition capable of controlled release of compounds having antimicrobial activity is provided.

This invention relates to a method for releasing a compound having antimicrobial activity from a matrix at a controlled rate, which comprises incorporating an enzyme and a substrate in said matrix beforehand to allow said enzyme and said substrate to react with each other in said matrix to thereby produce said compound having antimicrobial activity; and further relates to a coating composition comprising a film-forming resin, an enzyme, and a substrate, said enzyme being capable of reacting with said substrate to produce a compound having antimicrobial activity.

35 Claims, 1 Drawing Sheet

METHOD FOR CONTROLLED RELEASE OF COMPOUNDS HAVING ANTIMICROBIAL ACTIVITY AND COATING COMPOSITION

TECHNICAL FIELD

The present invention relates to a method for controlled release of compounds having antimicrobial activity and to a coating composition.

PRIOR ART

Compounds having antimicrobial activity, inclusive of antifouling agents, antibacterial agents, antifungal agents, biocides, and biorepellents, are in broad use today. The importance of protecting various objects with such compounds against the attack of fouling organisms, bacteria, and fungi has increased greatly in recent years.

For example, structures in contact with seawater, for example ships, oceanic constructions, fish farming nets, buoys and industrial water systems, are constantly exposed to water inhabited by various organisms. Therefore, as time passes by, microorganisms such as bacteria and diatoms and, further, fouling organisms of larger size, for example such animals and plants as barnacles mussels and sea lettuce, adhere to and grow on said structures. When the surfaces of the structures exposed to seawater are covered with such marine organisms, there take place corrosion of the covered part; decreased marine fuel efficiency due to increased frictional resistance of the ship bottom against seawater; massive deaths of fishes and shellfishes or decreased working efficiency due to clogging of fish farming nets; and sinking buoys due to reduced buoyancy. It is therefore very important to apply an antifouling treatment to such structures exposed to seawater.

Meanwhile, as can be easily understood from the serious problem posed by an increasing incidence of nosocomial infection due to meticillin-resistant staphylococci, it is also very important to treat interior walls, fixtures, furnishings, upholstery, etc. against the growth of bacteria and fungi in order to protect the internal environment of hospitals, schools, and hotels against such microorganisms.

The antimicrobial technology for the structures exposed to seawater or the interior walls of a hospital, for instance, includes a method which comprises incorporating a compound having antimicrobial activity in the very object to be protected and a method which comprises coating the surface of an object with a coating composition containing a compound having antimicrobial activity.

For example, the conventional antifouling technology for structures exposed to seawater comprises coating the surface of structures with an antifouling paint containing a compound having antimicrobial activity. This antifouling paint is designed to release such a compound gradually from the film into water by utilizing its solubility to thereby provide a sustained antifouling effect.

As the technology for keeping the interior environment of hospitals, etc., against bacteria and fungi, it is common practice to apply a coating containing a compound having antibacterial/antifungul activity to the surface of the interior walls, fixtures, furnishings, upholstery, etc.

When an object is treated with a compound having antifouling or antibacterial/antifungal activity, it is of course expected that the effect of the treatment will be expressed steadily over as long a time as possible. However, according to the above technology comprising coating an object surface with a coating composition containing an antimicrobial compound itself, satisfactory effect is obtained only for a limited time period following the treatment. Even when the content of those active compound is high, the effect declines rapidly with time, thus failing to insure a sustained long-term effect. The demand therefore exists for a new methodology for insuring a sustained long-term effect.

There are many compounds having antimicrobial activity. As compounds having antifouling activity for incorporation in antifouling paints, organotin compounds have been mostly employed. Moreover, as described in Bohkin Bohbai Handbook [Handbook of Antibacterial and Antifungal Technologies (Japanese Society for Protection Against Bacteria and Fungi ed., Gihodo Publishing Co., 1986)], it is known that hydrogen peroxide shows high antimicrobial/biocidal activity against a broad spectrum of bacteria and other microorganisms. Furthermore, a variety of compounds such as aliphatic carboxylic acids, aromatic carboxylicacids, aliphatic alcohols, and phenolic compounds are also known to have antimicrobial activity.

However, as pointed out frequently, organotin compounds have high toxicity and, when formulated in antifouling paints, find their way into the seawater to contaminate the marine environment. In addition, the protection of workers against hazards adds to the difficulty of use of those compounds.

Hydrogen peroxide is highly safe and free from the above problems. Because hydrogen peroxide is an unstable compound, however, it has been practically impossible to use it directly as an ingredient in antifouling or antibacterial/antifungal paints.

Aliphatic carboxylic acids, aromatic carboxylic acids, aliphatic alcohols, and phenolic compounds are free from safety and pollution problems just as is hydrogen peroxide. However, when those compounds are directly formulated into an antifouling paint and applied to the structures in water, they are eluted from the films into the surrounding water in a very brief period of time because of their highly solubility fir water. It is thus impossible to maintain an elution level necessary for displaying antifouling property for a long period of time. When these compounds are formulated into an antibacterial/antifungal paint and applied to the interior walls of hospitals, they are readily evaporated off or driven off by the water contained in the atmosphere as it is the case with said antifouling paint. Thus it also fails to provide a long-term antibacterial/antifungal effect. Besides, carboxylic acids in general emanate intense foreign odors so that they are difficult to use just as are toxic compounds.

In the above state of the art, the present invention has for its object to provide a novel method for sustained release of compounds having antimicrobial activity and a coating composition capable of releasing a safe and effective compound having antimicrobial activity at a controlled rate.

SUMMARY OF THE INVENTION

The present invention relates to a method for releasing a compound having antimicrobial activity from a matrix at a controlled rate, which comprises incorporating an enzyme and a substrate in said matrix beforehand to allow said enzyme and said substrate to react with each other in said matrix to thereby produce said compound having antimicrobial activity.

The present invention further relates to a coating composition comprising a film-forming resin, an enzyme, and a substrate, said enzyme being capable of reacting with said substrate to produce a compound having antimicrobial activity.

DETAILED DESCRIPTION OF THE INVENTION

Figure 1:
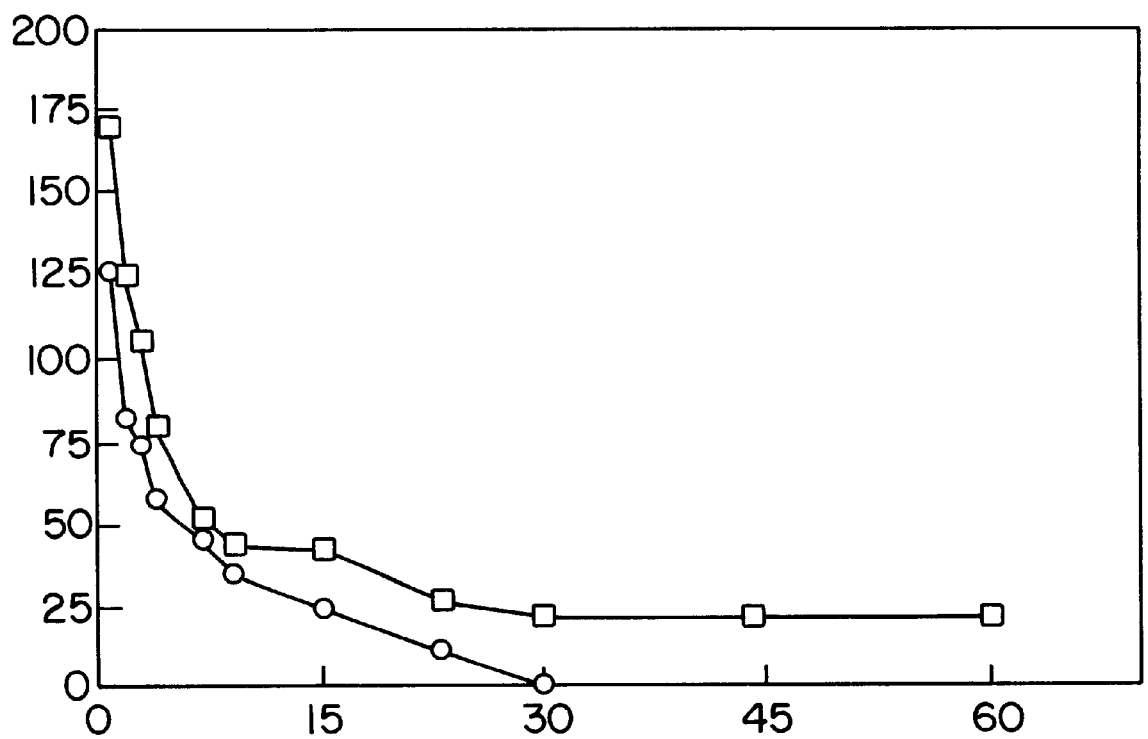
FIG. 1 is a diagrammatic representation of the amount of release versus the duration of release of butyric acid in Example 1 and Comparative Example 1, where the ordinate represents the amount of release of butyric acid ($\mu g/cm^2/day$) and the abscissa represents the duration of release (day).

The present invention is now described in detail.

According to the method for controlled release of a compound having antimicrobial activity according to the present invention, an enzyme and a substrate are incorporated in a matrix beforehand and allowed to react with each other in the matrix to thereby produce a compound having antimicrobial activity.

The matrix is not particularly restricted in kind but includes a paint film, a self-supporting film, a textile fabric, a synthetic resin film or sheet, and an inorganic wall paint, among others.

The compound having antimicrobial activity is not restricted, provided it is produced as the result of enzyme-substrate reaction. As such, there can be mentioned many compounds having antifouling activity, compounds having antibacterial/antifungal activity, compounds having biocidal activity, and compounds having biorepellent activity, etc.

As mentioned above, the compound having antimicrobial activity is produced by enzymatic reaction between an enzyme and a substrate. It should be understood that said compound having antimicrobial activity may be a compound obtained as the direct result of enzymatic reaction between the enzyme and the substrate or a compound formed from the product of such enzymatic reaction through further enzymatic or chemical reaction. The former case in which the compound having antimicrobial activity is the direct product of enzymatic reaction typically includes the case in which said substrate is a precursor of the compound having antimicrobial activity. Typical of the latter case in which the compound having antimicrobial activity is formed from such an enzymatic reaction product through further enzymatic or chemical reaction is the case in which such an enzymatic reaction product is a precursor of the objective compound having antimicrobial activity.

Furthermore, said compound having antimicrobial activity may be other than products whose major structural portions are originated from the substrate among the products obtained by said enzyme-substrate reaction. Falling into this category is the case in which the substrate is deaminated or oxidized/reduced by deamination or oxidation/reduction reaction to produce an amino-containing compound or a peroxide.

The above-mentioned compound having antimicrobial activity includes but is not limited to carboxyl group-containing compounds, hydroxyl group-containing compounds, amino group-containing compounds, aldehyde group-containing compounds, hydrogen peroxide, and decomposition products of chitosan.

The carboxyl group-containing compound is not particularly restricted in kind but includes a variety of organic acid compounds, e.g. aliphatic acids such as formic acid, acetic acid, propionic acid, butyric acid, caproic acid, caprylic acid, capric acid, lauric acid, myristic acid, palmitic acid, oleic acid, linoleic acid, linolenic acid, monochloroacetic acid, monofluoroacetic acid, sorbic acid, undecylenic acid, etc.; dibasic acids such as oxalic acid etc.; aromatic carboxylic acids such as benzoic acid, p-chlorobenzoic acid, p-hydroxybenzoic acid, salicylic acid, cinnamic acid, etc.; and their derivatives and halides.

There is no particular limitation on an enzyme-substrate combination capable of producing such a carboxyl group-containing compound. Typical are the case in which the enzyme is an esterase and the substrate is an ester bond-containing compound and the case in which the enzyme is an amidase and the substrate is an amide bond-containing compound.

The esterase is not particularly restricted in kind but includes esterases such as carboxylesterase, arylesterase, acetylesterase, etc.; lipases such as triacylglycerol lipase, lipoprotein lipase, etc.; and proteases such as subtilisin, chymotrypsin, tripsin, elastase, cathepsin, papain, chymopapain, pepsin, etc., and so forth.

The ester bond-containing compound mentioned above is not particularly restricted in kind but includes, among others, esters of any of said carboxyl group-containing compounds with aliphatic alcohols such as methyl alcohol, ethyl alcohol, propyl alcohol, butyl alcohol, pentyl alcohol, caproyl alcohol, caprylyl alcohol, capryl alcohol, lauryl alcohol, myristyl alcohol, palmityl alcohol, oleyl alcohol, etc.; esters of any of said carboxyl group-containing compounds with aromatic alcohols such as phenol, benzyl alcohol, etc.; esters of any of said carboxyl group-containing compounds with polyhydric alcohols such as ethylene glycol, glycerol, etc.; and esters of any of said carboxyl group-containing compounds with derivatives or halides of said aliphatic alcohols, aromatic alcohols, or polyhydric alcohols.

The ester bond-containing compound mentioned above is hydrolyzed by said esterase in the above-mentioned matrix to produce said carboxylic group-containing compound. This enzymatic reaction proceeds when water is present in the reaction system, as follows.

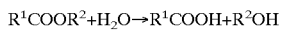

$$R^1COOR^2 + H_2O \rightarrow R^1COOH + R^2OH$$

In the above reaction schema, $R^1$ represents carboxylic residue and $R^2$ represents an alcohol residue. The water necessary for the above enzymatic reaction is supplied as follows. Thus, when the above matrix is present in the atmosphere, the water contained in the atmosphere migrates into the matrix to supply the necessary water to the reaction system. When the matrix exists in water such as seawater, the very water penetrates into the matrix to supply the necessary water to the reaction system. Therefore, even when said ester bond-containing compound and said esterase coexist in the matrix, the above-mentioned enzymatic reaction does not proceed unless water penetrates into the matrix, with the result that said carboxyl group-containing compound cannot be produced. On the other hand, when the matrix contacts air or seawater and consequently water finds its way into the matrix, the above enzymatic reaction proceeds, with the result that said carboxyl group-containing compound is produced in the matrix. Thus, in accordance with the present invention, said carboxyl group-containing compound is persistently produced within the matrix at a constant rate to obtain the objective controlled release.

The amidase mentioned above is not particularly restricted in kind but includes proteases such as chymotrypsin, trypsin, acrocin, elastase, subtilisin, cathepsin, proteinase, papain, physin, chymopapain, pepsin, chymosin, and so forth.

The amide bond-containing compound mentioned above is not particularly restricted in kind but includes, among others, amides of any of said carboxyl group-containing compounds with aliphatic amines such as butylamine, hexylamine, octylamine, decylamine, laurylamine, stearylamine, oleylamine, etc.; and amides of any said carboxyl group-containing compounds with aromatic amines such as aniline, toluidine, xylidine, and alkylanilines such as hexylaniline, octylaniline, nonylaniline, dodecylaniline, and so forth.

The hydroxyl group-containing compound mentioned above is not particularly restricted in kind but includes, among others, aliphatic alcohols such as methyl alcohol, ethyl alcohol, propyl alcohol, isopropyl alcohol, butyl alcohol, isobutyl alcohol, pentyl alcohol, isopentyl alcohol, hexyl alcohol, etc.; aromatic alcohols such as phenol, chlorophenol, and alkylphenols such as cresol, xylenol, etc., resorcinol, benzyl alcohol, etc.; and the derivatives and halides of said aliphatic or aromatic alcohols.

There is no particular limitation on an enzyme-substrate combination capable of producing the hydroxyl group-containing compound. Preferred is the case in which the enzyme is an esterase and the substrate is an ester bond-containing compound.

The esterase and the ester bond-containing compound are not particularly restricted in kind but each includes the species mentioned hereinbefore.

The amino group-containing compound mentioned above is not particularly restricted in kind, either, but includes aliphatic amines such as butylamine, hexylamine, octylamine, decylamine, laurylamine, stearylamine, oleylamine, cyclohexylamine, etc.; and aromatic amines such as aniline, toluidine, xylidine, p-n-hexylaniline, p-n-octylaniline, p-nonylaniline, p-dodecylaniline, and so forth.

There is no particular limitation on an enzyme-substrate combination capable of producing said amino group-containing compound. Preferred, however, is the case in which the enzyme is an amidase and the substrate is an amide bond-containing compound.

The amidase and the amide bond-containing compound are not particularly restricted in kind but each includes the species mentioned hereinbefore.

The aldehyde group-containing compound is not particularly restricted in kind but includes aliphatic aldehydes such as formaldehyde, glyoxal, succinaldehyde, glutaraldehyde, capronaldehyde, caprylaldehyde, caprinaldehyde, laurinaldehyde, stearinaldehyde, oleinaldehyde, etc.; benzaldehyde and its derivatives such as p-n-hexylbenzaldehyde, p-octylbenzaldehyde, p-oleylbenzaldehyde, vaniline, piperonal, etc.; salicylaldehyde, cinnamaldehyde, and so forth.

An enzyme-substrate combination capable of producing said aldehyde group-containing compound is not particularly restricted but includes the case in which the enzyme is alcohol dehydrogenase and the substrate is an aliphatic alcohol, e.g. methanol, ethanol, etc.; the case in which the enzyme is alcohol oxidase and the substrate is an aliphatic alcohol such as methanol, ethanol, etc.; the case in which the enzyme is arylalcohol dehydrogenase and the substrate is an aromatic alcohol such as phenol, cresol, etc.; and the case in which the enzyme is amine oxidase and the substrate is an aliphatic amine such as butylamine, hexylamine, and so forth.

An enzyme-substrate combination capable of producing hydrogen peroxide is not particularly restricted but preferably includes a combination such that the enzyme is an oxidase and the substrate is a compound to be oxidized by said oxidase.

A combination of said oxidase with said compound to be oxidized thereby is not particularly restricted but specifically includes such combinations as malate oxidase-malic acid; glucose oxidase-glucose; hexose oxidase-glucose; cholesterol oxidase-cholesterol; arylalcohol oxidase-arylalcohol: galactose oxidase-galactose; alcohol oxidase-alcohol; lathosterol oxidase-lathosterol; aspartate oxidase-aspartic acid; L-amino-acid oxidase-L-amino acid; D-amino-acid oxidase-D-amino acid; amine oxidase-amine; D-glutamate oxidase-glutamine; ethanolamine oxidase-ethanolamine; NADH oxidase-NADH; urate oxidase (uricase)-uric acid; superoxide dismutase-superoxide radical; and so forth.

The enzymatic reaction between said oxidase and its substrate compound yields hydrogen peroxide. As shown below, this enzymatic reaction proceeds when either oxygen or oxygen and water are present in the reaction system.

1) Compound A (substrate)+oxygen→Compound B (oxide of Compound A)+hydrogen peroxide
2) Compound C (substrate)+oxygen+water→Compound D+hydrogen peroxide+ammonium ion
3) Compound E (substrate)+oxygen+water→Compound F (oxide of Compound E)+hydrogen peroxide
4) Superoxide radical+proton→hydrogen peroxide+oxygen The above-mentioned oxygen is supplied not only from atmospheric air but also from seawater containing dissolved oxygen as the oxygen permeates into the matrix from its surface in contact with seawater or the like. Therefore, even in water such as seawater, the enzymatic reaction proceeds in the matrix as water penetrates into the matrix, with the result that hydrogen peroxide is produced in the matrix.

An enzyme-substrate combination capable of producing said decomposition product of chitosan is not particularly restricted. Preferred is the case in which the enzyme is a chitosan-decomposing enzyme and the substrate is chitosan.

The chitosan-decomposing enzyme is not particularly restricted in kind but includes chitosanase, cellulose, lysothyme, and so forth.

In the present invention, the enzyme for use as incorporated in the matrix may be any of a purified enzyme, a crude enzyme, or enzyme-containing cells. The source of the enzyme is not restricted, either, but includes microorganisms, plants, and animals. Moreover, in incorporating an enzyme in the matrix, the enzyme may be directly incorporated or it can be used after modification with another compound, or in the form of an immobilized enzyme. The specific forms of said modified enzyme and immobilized enzyme are not particularly restricted but include enzymes entrapped in reverse micelles; enzymes modified with lipids or surfactants; enzymes modified with polyethylene glycol; and enzymes immobilized on polymer matrices, among other forms.

Generally, enzymatic reaction between an enzyme and a substrate proceeds in the presence of water as the medium. Thus, even if both an enzyme and its substrate coexist, enzymatic reaction does not proceed unless they encounter each other through the water. In the method for controlled release of a compound having antibiotic activity according to the present invention, the controlled release of the compound having antimicrobial activity is achieved by exploiting the above characteristic of enzymatic reaction. Thus, an enzyme and its substrate occurring as dispersed in a matrix are brought into contact by the water penetrating into the matrix from the atmospheric air or other environment with the progress of time, thus beginning to react with each other to produce a compound having antimicrobial activity. In the present invention, the penetration of water into the matrix occurs gradually and sustainedly so that the compound having antimicrobial activity is produced persistently at a controlled rate, thus achieving controlled release of this compound.

Furthermore, in the method according to the invention, the stability of the matrix itself will not be impaired because only the selected ingredients in the composition of the matrix may be allowed to take part in enzymatic reaction. In addition, the objective compound can be steadily released in an effective amount since sufficiently high reactivity is assured at an ordinary temperature.

As described above, the compound having antimicrobial activity is produced within the matrix according to the method of the present invention. Therefore, even when this compound is highly soluble, unstable, or hard to handle, the inherent antimicrobial activity of the compound can be fully exploited. For example, it is by now possible to previously convert a highly water-soluble compound to an insoluble compound, an unstable compound to a stable compound, a toxic compound to a nontoxic compound, or a malodorous compound to an odorless compound, then incorporate the resulting compound in a matrix beforehand, and cause the objective compound to be produced by enzymatic reaction. In this manner, various compounds having antimicrobial activity that could not be exploited before can now be successfully utilized.

The method for controlled release of compounds having antimicrobial activity according to the present invention can be easily reduced to practice through the use of a coating composition of the invention, which is now described in detail.

Thus, the coating composition according to the present invention comprises a film-forming resin, an enzyme, and a substrate, said enzyme being capable of reacting with said substrate to produce a compound having antimicrobial activity.

The film-forming resin mentioned above is not particularly restricted in kind but includes, among others, acrylic resin, silicone resin, polyester resin, chloroprene rubber, vinyl chloride resin, chlorinated polyethylene resin, chlorinated polypropylene resin, styrene-butadiene copolymer resin, epoxy resin, polyamide resin, petroleum resin, wax, paraffin, rosin ester, rosin-based resin; and a resin containing a metal element such as tin, copper, or zinc in the side chain. Those resins can be used alone or in combination.

The above-mentioned film-forming resin is formulated with a solvent and optional additives. As such formulating agents, those not interfering with enzymatic reaction can be selected from among the ingredients used in the conventional coating composition.

The solvent mentioned above includes various organic solvents such as xylene and toluene.

The additives mentioned above may for example be plasticizers, coloring agents, and extenders.

The coating composition of the present invention is produced by adding an enzyme and a substrate to the above film-forming resin. The enzyme and the substrate are selected according to the desired characteristics of the product compound having antibacterial/antifungal or antifouling activity. In this operation, said substrate may be formulated as an ingredient independent of said film-forming resin or have been previously coupled to said film-forming resin through chemical linkage which is cleaved on enzymatic reaction.

There is no particular limitation on the method for adding the enzyme. For example, the enzyme may be added directly to said film-forming resin or optionally added as in the form of said modified enzyme or immobilized enzyme.

In the present invention, the formulating amount of the enzyme can be judiciously set according to the desired release kinetics of the compound having antimicrobial activity.

There is no particular limitation on the method for producing the coating composition of the invention. Thus, after addition of said enzyme and substrate to said film-forming resin, the mixture can be processed into a coating composition according to the conventional paint production technology typically employing a high-speed dispersing machine.

The preferred modes of application of the method of the present invention are now described.

The method for controlled release of a compound having antimicrobial activity according to the present invention can be applied with advantage for the controlled release of a compound having antibacterial and/or antifungal activity.

In this application, the surface of an object exposed to air is coated with the coating composition of the invention to cause controlled production of the compound having antibacterial/antifungal activity within the resulting film.

The above-mentioned object exposed to air is not particularly restricted in kind but includes any such object requiring an antibacterial/antifungal treatment. Specifically, the interior walls and floors of buildings such as hospitals, schools, and hotels; furnishings such as beds, lockers, etc.; and textile articles such as operating gowns, gloves, and masks can be typically mentioned.

The above-mentioned compound having antibacterial/antifungal activity is produced sustainedly at a constant rate as the enzyme and substrate in the paint film reacts with each other, so that the film provides satisfactory antibacterial/antifungal effect in a steady manner for an extended period of time. Therefore, nosocomial infections due to meticillin-resistant staphylococci and other pathogenic microorganisms can be effectively prevented.

As the compound having antibacterial and/or antifungal activity, a suitable member selected from among the specific compounds mentioned hereinbefore can be selectively employed.

The method for controlled release of the compound having antimicrobial activity according to the present invention can be applied with advantage to the controlled release of a compound having antifouling activity.

In this application, the surface of a structure contact with water is coated with the coating composition of the invention so as to let the antifoulant compound be produced in the paint film and released into water.

The structure mentioned above may be any structure at least a portion of which has a surface contacting water such as seawater and requiring protection from attachment of aquatic life. Specifically, there can be mentioned the ship bottom, seaport facilities, buoys, pipelines, bridges, seabed stations, fish farming nets, stationary nets, submarine oil field facilities, power station water conduits, industrial water facilities, bulwarks, moorings, etc.

The paint film is formed on the surfaces of such equipment which are to be protected against fouling. The compound having antifouling activity is persistently produced at a constant rate by reaction between an enzyme and its substrate within the paint film. The antifoulant compound so produced is released into the ambient water to achieve controlled release. As the compound having antifouling activity, a suitable member selected from the species mentioned hereinbefore is employed.

According to the method for controlled release of compounds having antimicrobial activity and the associated coating composition according to the present invention, the constitutions of which have been described above, those antimicrobial compounds which have never been exploited before can now be utilized with advantage to provide a sustained long-term release of the compounds.

BEST MODE FOR CARRYING OUT THE INVENTION

The following examples are presented to illustrate the present invention in further detail and should by no means be construed as defining the scope of the invention.

EXAMPLE 1

To 50 g of a solution of poly(methyl methacrylate) (Mn=ca 14000) in xylene (NV=35%) were added 7.5 g of tributyrin and 0.5 g of lipase (derived from *Rhizopus niveus*; Nagase Biochemical Industries), and using a high-speed Disper, the mixture was sufficiently agitated and dispersed. The resulting resin composition was applied to a poly(vinyl chloride) sheet in a wet thickness of 600 $\mu$m (5.5 cm×5.5 cm) and dried at room temperature for 3 days. This coated sheet was immersed in 30 ml of 20-mM phosphate buffer (pH 7.0) and incubated at 25° C. The buffer solution was changed from time to time and the amounts of butyric acid released from the resin film ($\mu$g/cm$^2$/day) were determined by liquid chromatography. The result is shown (□) in FIG. 1.

COMPARATIVE EXAMPLE 1

To 50 g of the same xylene solution of poly(methyl methacrylate) as above was added 4.37 g of butyric acid and the mixture was stirred well to provide a resin composition. Otherwise, the procedure of Example 1 was repeated and the amounts of butyric acid released from the resin film were determined with time. The result is shown (○) in FIG. 1.

It is apparent from FIG. 1 that, in Example 1, butyric acid was released in substantially constant amounts for sufficient expression of antimicrobial activity even after 60 days. On the other hand, in Comparative Example 1, the amount of butyric acid eluted became insufficient for expression of antimicrobial activity in approximately 15 days and substantially no butyric acid was released after 30 days.

EXAMPLE 2

To 50 g of a solution of hydroxyethyl methacrylate homopolymer (Mn=ca 15000) in ethanol (NV=40%) were added 4 g of cholesterol and 0.2 g of cholesterol oxidase (derived from a Pseudomonas strain, Wako Pure Chemical Industries), and using a high-speed Disper, the mixture was stirred well. The resulting resin composition was applied to a poly(vinyl chloride) sheet in a wet thickness of 400 $\mu$m (2 cm×1.5 cm) and dried at room temperature for 3 days. This coated sheet was immersed in 50 mM phosphate buffer (pH 7.5) and incubated at 30° C. for 22 hours. The rate of release of hydrogen peroxide released from the cast film into the buffer (nmol/cm$^2$/day) was determined by the o-dianisidine-peroxidase method (F. W. Janssen and H. W. Ruelius, Biochim. Biophys. Acta, 151, 330–342, 1968). The result is shown in Table 1.

EXAMPLE 3

Except that a solution of hydroxyethyl methacrylate (HEMA)/methyl methacrylate (MMA) copolymer (copolymerization ratio HEMA/MMA=3/1, Mn=ca 14000) in ethanol (NV=40%) was used, the procedure of Example 2 was otherwise repeated and the rate of release of hydrogen peroxide from the resin film was determined as in Example 2. The result is shown in Table 1.

TABLE 1

|  | Example 2 | Example 3 |
| --- | --- | --- |
| Rate of release of hydrogen peroxide (nmol/cm$^2$/day) | 21 | 15 |

EXAMPLE 4

To 50 g of a solution of poly(methyl methacrylate) (Mn=ca 14000) in xylene (NV=35%) were added 7.5 g of tricaprin and 0.5 g of lipase (SP523, Novo-Nordisk Bioindustries), and using a high-speed Disper, the mixture was sufficiently agitated and dispersed to provide an antifouling paint composition. A 300×100 mm test steel sheet precoated with an anticorrosive paint was coated with the above antifouling paint composition in a dry thickness of 60–80 $\mu$m, followed by one-day-long drying, to provide an antifouling-coated steel sheet. Using this sheet, the antifouling performance of the coating film was evaluated.

Evaluation of the Antifouling Effect of the Paint Film

The antifouling paint-coated steel sheet was immersed in seawater to a depth of 1 m from an offshore experimental raft in Tamano-shi, Okayama-ken, Japan. After one, two and three months of immersion, the coated surface was visually examined to check the degree of fouling by slime comprising microorganisms. The result is shown in Table 2.

COMPARATIVE EXAMPLE 2

To 50 g of the same xylene solution of poly(methyl methacrylate) as above was added 4.66 g of capric acid and the mixture was sufficiently agitated and dispersed to provide an antifouling paint composition. Except that the above antifouling paint composition was used, the procedure of Example 4 was otherwise repeated for the evaluation of the antifouling effect of the film. The result is shown in Table 2.

TABLE 2

|  | Immersion time (months) | | |
| --- | --- | --- | --- |
|  | 1 | 2 | 3 |
| Example 4 | ◎ | ◎ | ◎ |
| Comparative Example 2 | ◎ | ○ | X |

◎: no slimy fouling
○: slight slimy fouling
X: slimy fouling all over

What is claimed is:

1. A method for releasing a compound having antimicrobial activity from a matrix at a controlled rate, which comprises incorporating an enzyme and a substrate in said matrix beforehand to allow said enzyme and said substrate to react with each other in said matrix to thereby produce said compound having antimicrobial activity, wherein said matrix is a paint film on the surface of an object exposed to air and said compound having antimicrobial activity is a compound having antibacterial and/or antifungal activity, and said substrate is at least one member selected from the group consisting of an ester bond-containing compound, an amide bond-containing compound, aliphatic alcohol, aromatic alcohol, aliphatic amine, and chitosan.

2. A method for releasing a compound having antimicrobial activity from a matrix at a controlled rate which comprises incorporating an enzyme and a substrate in said matrix beforehand to allow said enzyme and said substrate to react with each other in said matrix to thereby produce said compound having antimicrobial activity, wherein said matrix is a paint film on the surface of structures exposed to water and said compound having antimicrobial activity is a compound having antifouling activity which is to be released into said water, and said substrate is at least one member selected from the group consisting of an ester bond-containing compound, an amide bond-containing compound, aliphatic alcohol, aromatic alcohol, aliphatic amine, and chitosan.

3. The method for releasing a compound having antimicrobial activity from a matrix at a controlled rate according to claim 1 or 2, wherein said compound having antimicrobial activity is a carboxyl group-containing compound.

4. The method for releasing a compound having antimicrobial activity from a matrix at a controlled rate according to claim 3, wherein said enzyme is an esterase and said substrate is an ester bond-containing compound.

5. The method for releasing a compound having antimicrobial activity from a matrix at a controlled rate according to claim 3, wherein said enzyme is an amidase and said substrate is an amide bond-containing compound.

6. The method for releasing a compound having antimicrobial activity from a matrix at a controlled rate according to claim 1 or 2, wherein said compound having antimicrobial activity is a hydroxyl group-containing compound.

7. The method for releasing a compound having antimicrobial activity from a matrix at a controlled rate according to claim 6, wherein said enzyme is an esterase and said substrate is an ester bond-containing compound.

8. The method for releasing a compound having antimicrobial activity from a matrix at a controlled rate according to claim 1 or 2, wherein said compound having antimicrobial activity is an amino group-containing compound.

9. The method for releasing a compound having antimicrobial activity from a matrix at a controlled rate according to claim 8, wherein said enzyme is an amidase and said substrate is an amide bond-containing compound.

10. The method for releasing a compound having antimicrobial activity from a matrix at a controlled rate according to claim 1 or 2, wherein said compound having antimicrobial activity is an aldehyde group-containing compound.

11. The method for releasing a compound having antimicrobial activity from a matrix at a controlled rate according to claim 10, wherein said enzyme is an alcohol dehydrogenase and said substrate is an aliphatic alcohol.

12. The method for releasing a compound having antimicrobial activity from a matrix at a controlled rate according to claim 10, wherein said enzyme is an aryl alcohol dehydrogenase and said substrate is an aromatic alcohol.

13. The method for releasing a compound having antimicrobial activity from a matrix at a controlled rate according to claim 1 or 2, wherein said compound having antimicrobial activity is a decomposition product of chitosan, said enzyme is a chitosan-decomposing enzyme, and said substrate is chitosan.

14. The method for releasing a compound having antimicrobial activity from a matrix at a controlled rate according to claim 2, wherein said compound having antimicrobial activity is a carboxyl group-containing compound.

15. The method for releasing a compound having antimicrobial activity from a matrix at a controlled rate according to claim 14, wherein said enzyme is an esterase and said substrate is an ester bond-containing compound.

16. The method for releasing a compound having antimicrobial activity from a matrix at a controlled rate according to claim 14, wherein said enzyme is an amidase and said substrate is an amide bond-containing compound.

17. The method for releasing a compound having antimicrobial activity from a matrix at a controlled rate according to claim 2, wherein said compound having antimicrobial activity is a hydroxyl group-containing compound.

18. The method for releasing a compound having antimicrobial activity from a matrix at a controlled rate according to claim 17, wherein said enzyme is an esterase and said substrate is an ester bond-containing compound.

19. The method for releasing a compound having antimicrobial activity from a matrix at a controlled rate according to claim 2, wherein said compound having antimicrobial activity is an amino group-containing compound.

20. The method for releasing a compound having antimicrobial activity from a matrix at a controlled rate according to claim 19, wherein said enzyme is an amidase and said substrate is an amide bond-containing compound.

21. The method for releasing a compound having antimicrobial activity from a matrix at a controlled rate according to claim 2, wherein said compound having antimicrobial activity is an aldehyde group-containing compound.

22. The method for releasing a compound having antimicrobial activity from a matrix at a controlled rate according to claim 21, wherein said enzyme is an alcohol dehydrogenase and said substrate is an aliphatic alcohol.

23. The method for releasing a compound having antimicrobial activity from a matrix at a controlled rate according to claim 21, wherein said enzyme is an aryl alcohol dehydrogenase and said substrate an aromatic alcohol.

24. The method for releasing a compound having antimicrobial activity from a matrix at a controlled rate according to claim 2, wherein said compound having antimicrobial activity is a decomposition product of chitosan, said enzyme is a chitosan-decomposing enzyme, and said substrate is chitosan.

25. The method for releasing a compound having antimicrobial activity from a matrix at a controlled rate according to claim 1, wherein said aliphatic alcohol is methanol or ethanol, said aromatic alcohol is phenol or cresol, and said aliphatic amine is butylamine or hexylamine.

26. The method for releasing a compound having antimicrobial activity from a matrix at a controlled rate according to claim 2, wherein said aliphatic alcohol is methanol or ethanol, said aromatic alcohol is phenol or cresol, and said aliphatic amine is butylamine or hexylamine.

27. The method for releasing a compound having antimicrobial activity from a matrix at a controlled rate according to claim 1, wherein said enzyme is at least one member selected from the group consisting of an esterase, an amidase, an alcohol dehydrogenase, an aryl alcohol dehydrogenase, and a chitosan-decomposing enzyme.

28. The method for releasing a compound having antimicrobial activity from a matrix at a controlled rate according to claim 2, wherein said enzyme is at least one member selected from the group consisting of an esterase, an amidase, an alcohol dehydrogenase, an aryl alcohol dehydrogenase, and a chitosan-decomposing enzyme.

29. A coating composition comprising a film-forming resin, an enzyme, and a substrate, wherein said film-forming resin is a paint film-forming resin and said enzyme reacts with said substrate to produce a compound having antimicrobial activity, and wherein said substrate is at least one member selected from the group consisting of an ester bond-containing compound, an amide bond-containing compound, aliphatic alcohol, aromatic alcohol, aliphatic amine, and chitosan.

30. The coating composition according to claim 29, wherein said compound having antimicrobial activity is a compound having antibacterial and/or antifungal activity.

31. The coating composition according to claim 29, wherein said compound having antimicrobial activity is a compound having antifouling activity.

32. The coating composition according to claim 29, 15 or 16 wherein said enzyme is an esterase and said substrate is an ester bond-containing compound.

33. The coating composition according to claim 29, 15 or 16, wherein said enzyme is an amidase and said substrate is an amide bond-containing compound.

34. The coating composition according to claim 29, 30 or 31 wherein said enzyme is a chitosan-decomposing enzyme and said substrate is chitosan.

35. The coating composition according to claim 29, wherein said enzyme is at least one member selected from the group consisting of an esterase, an amidase, an alcohol dehydrogenase, an aryl alcohol dehydrogenase, and a chitosan-decomposing enzyme.

\* \* \* \* \*

UNITED STATES PATENT AND TRADEMARK OFFICE
CERTIFICATE OF CORRECTION

PATENT NO. : 6,150,146
DATED : November 21, 2000
INVENTOR(S): Ryoji Hamade et al.

It is certified that error appears in the above-identified patent and that said Letters Patent is hereby corrected as shown below:

Title page, Item [22] should read:

---Filed: Mar. 17, 1998---

Signed and Sealed this

First Day of May, 2001

Attest:

NICHOLAS P. GODICI

*Attesting Officer*     *Acting Director of the United States Patent and Trademark Office*